US012654022B2

(12) United States Patent
Rosenberg et al.

(10) Patent No.: US 12,654,022 B2
(45) Date of Patent: Jun. 16, 2026

(54) RESPIRATORY GATED SHOCK DELIVERY BY SUBCUTANEOUS-IMPLANTABLE MEDICAL DEVICE

(71) Applicant: Pacesetter, Inc., Sylmar, CA (US)

(72) Inventors: Stuart Rosenberg, Woodbury, MN (US); Gene A. Bornzin, Simi Valley, CA (US); Wenwen Li, Stevenson Ranch, CA (US); Xiaoyi Min, Sylmar, CA (US)

(73) Assignee: Pacesetter, Inc., Sylmar, CA (US)

( * ) Notice: Subject to any disclaimer, the term of this patent is extended or adjusted under 35 U.S.C. 154(b) by 619 days.

(21) Appl. No.: 16/295,947

(22) Filed: Mar. 7, 2019

(65) Prior Publication Data

US 2020/0282226 A1     Sep. 10, 2020

(51) Int. Cl.
| | |
|---|---|
| *A61N 1/00* | (2006.01) |
| *A61B 5/0538* | (2021.01) |
| *A61B 5/085* | (2006.01) |
| *A61B 5/318* | (2021.01) |
| *A61N 1/39* | (2006.01) |

(52) U.S. Cl.
CPC .......... *A61N 1/3987* (2013.01); *A61B 5/0538* (2013.01); *A61B 5/086* (2025.01); *A61B 5/318* (2021.01); *A61N 1/3925* (2013.01); *A61N 1/3956* (2013.01); *A61B 2562/0219* (2013.01)

(58) Field of Classification Search
CPC ....... A61B 5/0205; A61N 1/3987; A61N 1/36
USPC .......................................................... 607/20
See application file for complete search history.

(56) References Cited

U.S. PATENT DOCUMENTS

| | | | | |
|---|---|---|---|---|
| 4,596,251 A | * | 6/1986 | Plicchi ............... | A61N 1/36521 |
| | | | | 600/536 |
| 4,884,576 A | * | 12/1989 | Alt ...................... | A61N 1/36521 |
| | | | | 607/18 |
| 5,800,470 A | * | 9/1998 | Stein .................. | A61N 1/36514 |
| | | | | 607/20 |
| 6,141,590 A | * | 10/2000 | Renirie .............. | A61N 1/36521 |
| | | | | 607/18 |
| 6,208,900 B1 | * | 3/2001 | Ecker ................. | A61N 1/36542 |
| | | | | 607/17 |

(Continued)

FOREIGN PATENT DOCUMENTS

WO     WO-2017196477 A1 * 11/2017

*Primary Examiner* — William J Levicky
*Assistant Examiner* — Anant A Gupta
(74) *Attorney, Agent, or Firm* — Dean D. Small; Carroll, Hoette & Butscher, LLC

(57) ABSTRACT

A method and system for managing delivery of a respiration gated defibrillation shock from a subcutaneous implantable medical device (S-IMD) having one or more extra vascular electrodes. The method and system sense cardiac events of a heart. Additionally, the method and system utilize one or more processors to declare a shockable arrhythmia based on the cardiac events, obtain a respiration proxy signal indicative of respiration, track a respiration state related (RSR) characteristic from the respiration proxy signal, gate delivery of a high voltage (HV) shock based on occurrence of a respiration-gated (RG) trigger in connection with the RSR characteristic, and deliver the HV shock along a shocking vector between extra vascular electrodes based on the RG trigger to time delivering of the HV shock to occur during the select state within the respiration cycle.

20 Claims, 7 Drawing Sheets

(56)                    References Cited

U.S. PATENT DOCUMENTS

| | | | | |
|---|---|---|---|---|
| 7,302,295 | B2 * | 11/2007 | Stahmann | A61N 1/3601 |
| | | | | 128/200.24 |
| 7,539,539 | B1 * | 5/2009 | Bharmi | A61B 5/0452 |
| | | | | 600/529 |
| 8,626,292 | B2 * | 1/2014 | McCabe | A61B 5/4041 |
| | | | | 607/18 |
| 2006/0069326 | A1 * | 3/2006 | Heath | A61H 31/005 |
| | | | | 601/41 |
| 2008/0294215 | A1 * | 11/2008 | Sathaye | A61N 1/36521 |
| | | | | 607/20 |
| 2010/0016749 | A1 * | 1/2010 | Atsma | A61B 5/4818 |
| | | | | 600/529 |
| 2013/0218219 | A1 * | 8/2013 | Livnat | A61N 1/3956 |
| | | | | 607/6 |
| 2013/0261716 | A1 * | 10/2013 | Bardy | A61N 1/0504 |
| | | | | 607/116 |
| 2015/0142069 | A1 * | 5/2015 | Sambelashvili | A61N 1/3688 |
| | | | | 607/18 |
| 2015/0258344 | A1 * | 9/2015 | Tandri | A61N 1/395 |
| | | | | 607/4 |
| 2016/0256692 | A1 * | 9/2016 | Baru | A61N 1/36053 |
| 2017/0056669 | A1 * | 3/2017 | Kane | A61N 1/36521 |
| 2017/0095670 | A1 * | 4/2017 | Ghaffari | A61B 5/0024 |
| 2018/0221677 | A1 * | 8/2018 | Grinberg | A61N 1/3925 |
| 2018/0326215 | A1 * | 11/2018 | Ghosh | A61N 1/3756 |
| 2020/0046989 | A1 * | 2/2020 | Thompson-Nauman | |
| | | | | A61N 1/3925 |

* cited by examiner

RESPIRATORY GATED SHOCK DELIVERY BY SUBCUTANEOUS-IMPLANTABLE MEDICAL DEVICE

BACKGROUND

Embodiments of the present disclosure relate generally to subcutaneous implantable medical systems and methods, and more particularly to medical devices having pulse generators and leads that are implanted subcutaneously.

Currently, implantable medical devices (IMD) are provided for a variety of cardiac applications. IMDs may include a "housing" or "canister" (or "can") and one or more electrically-conductive leads that connect to the canister through an electro-mechanical connection. IMDs may contain electronics (e.g., a power source, microprocessor, capacitors, etc.) that control electrical activation of the leads to provide various functionalities. For instance, the IMD may be configured for pacemaking, cardioversion, and/or defibrillation. The IMD may also be designed to monitor heart rate, recognize certain events (e.g., ventricular fibrillation or ventricular tachycardia), and deliver electrical shock to reduce the risk of sudden cardiac death (SCD) from these events. The IMD may be used for patients who have already experienced potentially life-threatening events or for those that are at risk of SCD. The IMD may include a pulse generator and one or more leads having electrodes that may be used to detect how the heart is functioning or provide electrical shock to the heart.

One type of IMD delivers therapy through transvenous leads that are advanced to the right ventricle for detection and treatment of tachyarrhythmia. Transvenous IMDs (or TV-IMDs) may also provide bradycardia-pacing support. Although TV-IMDs can be helpful and prevent sudden cardiac death, TV-IMDs may have certain drawbacks or potential complications. For instance, it can be difficult and time-consuming to achieve venous access, thereby prolonging the medical procedure. TV-IMDs can be associated with hemopericardium, hemothorax, pneumothorax, lead dislodgement, lead malfunction, device-related infection, and venous occlusion. Transvenous leads may also malfunction through conductor failure in the leads or breaches in the insulation that surrounds the conductors.

A second type of IMD, referred to as a subcutaneous IMD (or S-IMD), uses an electrode configuration that can reside entirely within the subcutaneous space. The pulse generator is positioned along a side of the patient's chest below the arm pit (e.g., over the sixth rib near the left mid-axillary line). A lead extends from the pulse generator along the side of the patient toward the sternum. The lead then turns to extend parallel to the mid-sternal line and is positioned adjacent to the sternum extending between the xiphoid process and the manubriosternal junction. This portion of the lead includes a shock coil that is flanked by two sensing electrodes. The sensing electrodes sense the cardiac rhythm and the shock coil delivers counter-shocks through the subcutaneous tissue of the chest wall. Unlike the transvenous types, the S-IMDs lack intravenous and intracardiac leads and, as such, are less likely to have the noted complications associated with more invasive devices. Current electrode configurations for S-IMDs, however, have some challenges or undesirable features. For instance, S-IMDs typically have a conventional commercially available as IMDs are relatively large and exhibit higher defibrillation threshold (DFTs), as compared to modern transvenous S-IMDs. For example, a conventional S-IMD may be 60-70 mL in volume, as compared to a 30 mL transvenous S-IMD.

As another example, a conventional S-IMD may utilize DFTs of 80 J, as compared to 40 J for transvenous S-IMDs.

Additionally, it is well established that defibrillation performance is dependent on appropriate electrode placement. Electrode placement influences two primary factors that determine DFT. The first factor is field, the amount of current driven through the myocardium. The second factor is impedance, increased by subcutaneous fat around the shock coil or can electrodes.

Accordingly, a need remains to further improve upon the energy demands of conventional S-IMDs and for alternative S-IMD electrode configurations that provide an improved safety margin by increasing the probability of a successful electrode placement and defibrillation.

SUMMARY

In accordance with embodiments herein, a method for managing delivery of a respiration gated defibrillation shock from a subcutaneous implantable medical device (S-IMD) is provided. The S-IMD has one or more extra vascular electrodes. The method senses cardiac events of a heart. The method utilizes one or more processors to declare a shockable arrhythmia based on the cardiac events, and obtain a respiration proxy signal indicative of respiration. The respiration proxy signal varies over a respiration cycle. The method tracks a respiration state related (RSR) characteristic from the respiration proxy signal and gates delivery of a high voltage (HV) shock based on occurrence of a respiration-gated (RG) trigger in connection with the RSR characteristic. The RG trigger corresponding to a point in time when the RSR characteristic indicates a select state within the respiration cycle. The method delivers the HV shock along a shocking vector between extra vascular electrodes based on the RG trigger to time delivery of the HV shock to occur during the select state within the respiration cycle.

Optionally, the RSR characteristic may comprise a slope of the respiration proxy signal. The RG trigger may occur when the slope transitions from a negative value to a positive value. The slope transition may correspond to a point in the respiration proxy signal indicative of peak expiration. The RSR characteristic may represent a peak to peak amplitude range of one or more breaths. The RG trigger may occur when a current level of the respiration proxy signal falls a select amplitude drop below an amplitude corresponding to peak inspiration. The select amplitude drop may correspond to a percentage of the peak to peak amplitude range of one or more breaths. The RSR characteristic may represent a minimum amplitude of the respiration proxy signal. The RG trigger may occur when a current level of the respiration proxy signal falls to a select window surrounding the minimum amplitude of the respiration proxy signal corresponding to peak expiration.

Optionally, the RSR characteristic may represent a respiratory period. The RG trigger may occur when a time period, that may correspond to the respiratory period, elapses following a peak expiration of a most recent breath. The RSR characteristic may represent a respiratory period. The RG trigger may occur when a time period, that may correspond to a select amount of the respiratory period, elapses following a peak inspiration of a most recent breath. The method may measure the signal indicative of respiration during normal sinus rhythm to obtain at least one of a baseline peak to peak (P-P) range or a baseline respiratory period. The method may define a time out value based on the respiratory period. The gating may further comprise setting a timer based on the timeout value and initiating the timer in connection with the declaring the shockable arrhythmia. The delivering may comprise initiating delivery of the HV shock in response to expiration of the timer independent of whether the RG trigger occurs.

Optionally, the method may obtain at least one of thoracic impedance measurements or cardiogenic impedance measurements indicative of a respiratory cycle and may obtain the at least one of the estimated respiration depth or respiration phase from the respiratory cycle. The method may obtain wideband electrogram signals, may filter the electrogram signals for a low frequency content indicative of a respiratory cycle, and may obtain the at least one of the estimated respiration depth or respiration phase from the respiratory cycle. The method may obtain an accelerometer signal from an accelerometer, may filter the accelerometer signal to obtain a low frequency motion component indicative of a respiratory cycle, and may obtain the at least one of the estimated respiration depth or respiration phase from the respiratory cycle.

In accordance with embodiments herein, an implantable medical system is provided. The system comprises subcutaneous electrodes that are configured to be implanted at extra vascular positions. At least a portion of the electrodes are configured to sense cardiac events and are configured to define a shocking vector. An implantable medical device (IMD) is provided. The IMD comprises memory and one or more processors. The memory stores program instructions. One or more processors are configured to declare a shockable arrhythmia based on the cardiac events, and obtain a respiration proxy signal indicative of respiration. The respiration proxy signal varies over a respiration cycle. The system tracks a respiration state related (RSR) characteristic from the respiration proxy signal. The system gates delivery of a high voltage (HV) shock based on occurrence of a respiration-gated (RG) trigger in connection with the RSR characteristic. The RG trigger corresponds to a point in time when the RSR characteristic indicates a select state within the respiration cycle. The system delivers the HV shock along a shocking vector between shocking electrodes based on the RG trigger to time delivering of the HV shock to occur during the select state within the respiration cycle.

Optionally, the RSR characteristic may comprise a slope of the respiration proxy signal. The RG trigger may occur when the slope transitions from a negative value to a positive value. The slope transition may correspond to a point in the respiration proxy signal indicative of peak expiration. The RSR characteristic may represent a peak to peak amplitude range of one or more breaths. The RG trigger may occur when a current level of the respiration proxy signal falls a select amplitude drop below an amplitude corresponding to peak inspiration. The select amplitude drop may correspond to a percentage of the peak to peak amplitude range of one or more breaths. The RSR characteristic may represent a minimum amplitude of the respiration proxy signal. The RG trigger may occur when a current level of the respiration proxy signal falls to a select window surrounding the minimum amplitude of the respiration proxy signal corresponding to peak expiration.

Optionally, the RSR characteristic may represent a respiratory period. The RG trigger may occur when a time period, that may correspond to the respiratory period, elapses following a peak expiration of a most recent breath. The RSR characteristic may represent a respiratory period. The RG trigger may occur when a time period, that may correspond to a select amount of the respiratory period, elapses following a peak inspiration of a most recent breath. The system measures the signal indicative of respiration during normal sinus rhythm to obtain at least one of a baseline peak to peak (P-P) range or a baseline respiratory period. The system defines a time out value based on the respiratory period. The gating may comprise setting a timer based on the time out value and may initiate the timer in connection with the declaring the shockable arrhythmia. The delivering may comprise initiating delivery of the HV shock in response to expiration of the timer independent of whether the RG trigger occurs.

Optionally, the system may obtain at least one of thoracic impedance measurements or cardiogenic impedance measurements indicative of a respiratory cycle and may obtain the at least one of the estimated respiration depth or respiration phase from the respiratory cycle. The system may obtain wideband electrogram signals, and may filter the electrogram signals for a low frequency content indicative of a respiratory cycle, and may obtain the at least one of the estimated respiration depth or respiration phase from the respiratory cycle. The system may obtain obtaining an accelerometer signal from an accelerometer, and may filter the accelerometer signal to obtain a low frequency motion component indicative of a respiratory cycle, and may obtain the at least one of the estimated respiration depth or respiration phase from the respiratory cycle.

DETAILED DESCRIPTION

Figure 1A:
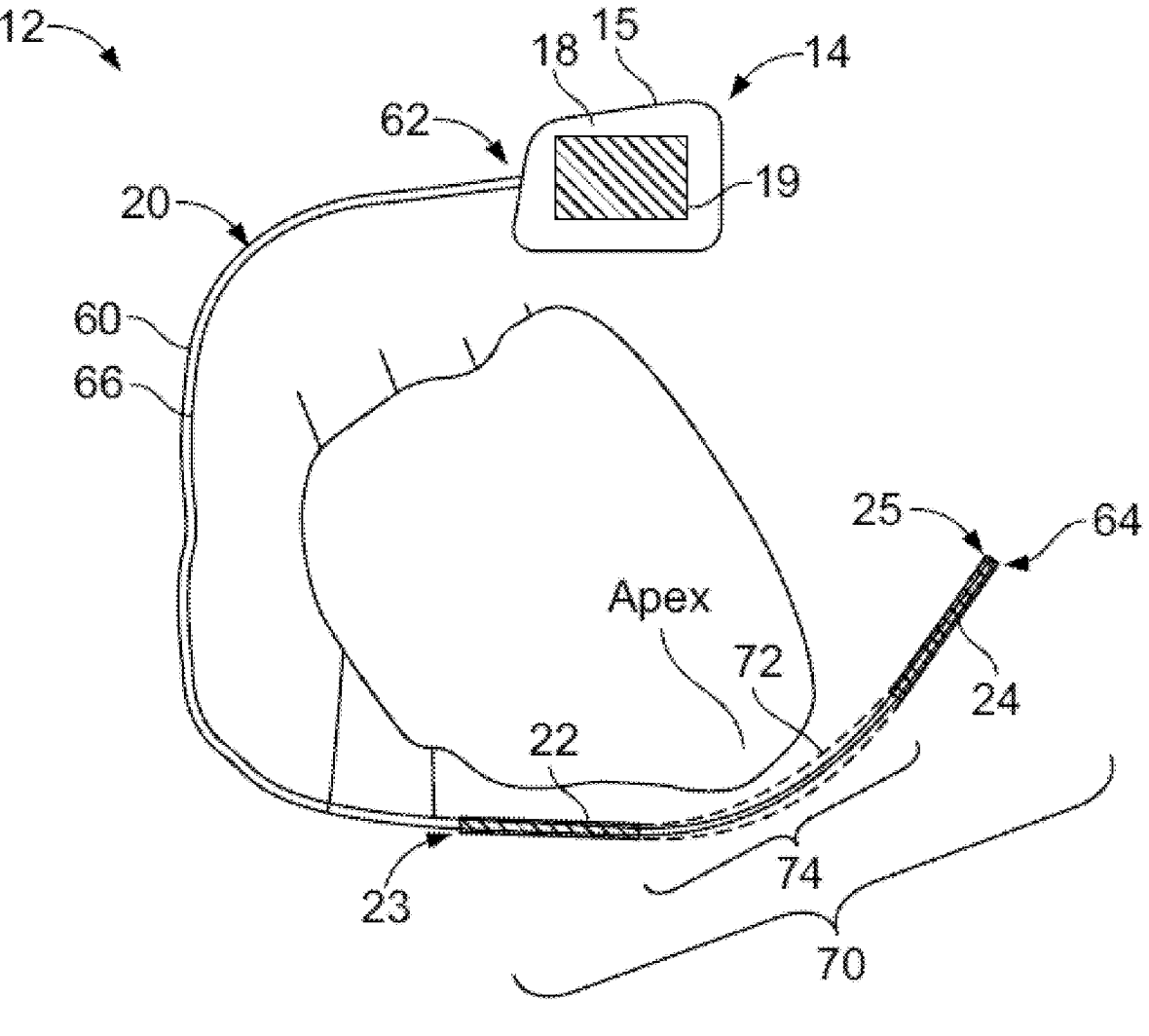
FIG. 1A illustrates a graphical representation of an implantable medical system that is configured to apply therapy to a heart in accordance with embodiments herein.

Embodiments set forth herein include (S-IMDs), systems that include S-IMD, and methods of using and positioning the same. In particular embodiments, the S-IMD includes a pulse generator (PG) that is positioned within a pectoral region of a chest of a patient. The PG has a housing or canister that includes a PG electrode. Embodiments also include at least one lead having first and second electrode segments with the first electrode segment positioned along an anterior of the chest of the patient and the second electrode segment positioned along a posterior of the patient. Optionally, embodiments may include additional electrode segments, such as a third or fourth electrode segment. For example, in some embodiments, the second electrode segment may comprise two electrode sub-segments.

The PG electrode and the first and second electrode segments may reliably provide a sufficient amount of energy for antiarrhythmic therapy (e.g., defibrillation). Embodiments may enable pulse generators with defibrillation thresholds (DFTs) that are less than known systems. For example, the DFT in some embodiments may be at most 50 Joules. The DFT in certain embodiments may be at most 45 Joules or, more particularly, at most 40 Joules. Embodiments may also enable using pulse generators or canisters with a smaller volume than known systems.

As used herein, the term "subcutaneously," when used to describe implanting a device (e.g., pulse generator, lead body, electrode, etc.), means implanting the device beneath the skin but above layers of skeletal muscle tissue, rib bones, and costal cartilage. The device is typically positioned under the subcutaneous tissue. When the term "subcutaneous" is used to characterize the entire implantable medical system, the term means that most of the operating components of the system (e.g., the pulse generator, shocking electrodes, optional sensing electrodes, lead bodies) or each and every one of the operating components is beneath the skin, but above layers of skeletal muscle tissue, rib bones, and costal cartilage. In some embodiments, however, one or more components may not be subcutaneous. For example, additional electrodes may be used that are transvenous or that contact outer cardiac tissue. In alternative embodiments, the pulse generator may be implanted submuscularly (e.g., under the serratus anterior muscle) or under the serratus anterior fascia but above muscle.

Embodiments herein may be implemented in connection with various types of implantable medical devices, such as the implantable medical devices described in U.S. patent application Ser. No. 15/973,219 "Implantable Medical Systems And Methods Including Pulse Generators And Leads," U.S. patent application Ser. No. 15/973,249 "Single-Site Implantation Methods For Medical Devices Having Multiple Leads," and U.S. patent application Ser. No. 15/973,195 "Subcutaneous Implantation Medical Device With Multiple Parasternal-Anterior Electrodes." The co-pending applications referenced herein are expressly incorporated herein by reference in their entireties.

FIG. 1A illustrates a graphical representation of an implantable medical system 12 that is configured to apply therapy to a heart. In particular embodiments, the system 12 may apply pacing therapy, cardiac resynchronization therapy (CRT), and general arrhythmia therapy, including defibrillation. The system 12 includes a subcutaneous implantable medical device (S-IMD) 14 that is configured to be implanted in a subcutaneous area exterior to the heart. The S-IMD 14 is positioned in a subcutaneous area or region.

In the illustrated embodiment, the system 12 includes only the S-IMD and is entirely or fully subcutaneous. The system 12 does not require insertion of a transvenous lead. It is contemplated, however, that system 12 may include other components. For example, alternative embodiments may include a transvenous lead or a leadless electrode.

The S-IMD 14 includes a pulse generator 15 and at least one lead 20 that is operably coupled to the pulse generator 15. The "at least one lead" is hereinafter referred to as "the lead." Nevertheless, it should be understood that the term, "the lead," may mean only a single lead or may mean more than one single lead. The lead 20 includes at least one electrode segment that is used for providing electrical shocks for defibrillation. Optionally, the lead 20 may include one or more sensing electrodes. The pulse generator 15 may be implanted subcutaneously and at least a portion of the lead 20 may be implanted subcutaneously. In particular embodiments, the S-IMD 14 is an entirely or fully subcutaneous S-IMD. In FIG. 1A, the S-IMD 14 is positioned within a pectoral region. Optionally, the S-IMD 14 may be positioned in a different subcutaneous region. The S-IMD 14 may detect or sense cardiac activity (e.g., cardiac rhythm). The S-IMD 14 is configured to deliver defibrillation therapy, based on the cardiac activity.

The pulse generator 15 includes a housing or canister 18. The pulse generator 15 is configured to be connected to the lead 20 of the system 12. The pulse generator 15 also includes a pulse-generator (PG) electrode 19. As used herein, a pulse generator or a housing of the pulse generator "includes an electrode" when the housing forms or constitutes the electrode or when the housing (or other part of the pulse generator) has a discrete electrode attached thereto. In particular embodiments, the housing 18 forms the PG electrode 19.

The lead 20 includes an elongated lead body 60 that extends from a PG-end portion 62 to a distal tip 64. The PG-end portion 62 is operably connected to the pulse generator 15 in FIG. 1A. The PG-end portion 62 may include one or more electrodes (not shown) that electrically engage respective terminals (not shown) of the pulse generator 15. More specifically, the PG-end portion 62 may be inserted into a port of the pulse generator 15 where the terminals are located.

The elongated lead body 60 includes an elongated flexible tube or sleeve 66 comprising, for example, a biocompatible material (e.g., polyurethane, silicone, etc.). The lead body 60 may include a single lumen (or passage) or multiple lumen (or passages) within the flexible tube 66. The lead 20 also includes a plurality of electrical conductors (not shown) that electrically couple the shocking electrode segments (and optionally sensing electrodes) to the pulse generator 15. The electrical conductors may be cabled conductors coated with PTFE (poly-tetrafluoroethylene) and/or ETFE (ethylenetetrafluoroethylene). The lead body 60 may be configured for receiving a stylet that enables positioning of the lead. The electrical conductors are terminated to the respective electrode segments. For example, the conductors may be terminated to respective electrodes of the PG-end portion 62 and then respective electrode segments 22, 24 (described below).

As described above, the lead 20 may include one or more electrode segments. As shown, the lead 20 includes electrode segments 22, 24 in which the electrode segments 22, 24 are spaced apart from one another having an electrical gap 74 therebetween. The lead body 60 may extend between the gap 74. The electrode segments 22, 24 may be referred to as first and second electrode segments 22, 24. The electrode segment 22 may be positioned along an anterior of the chest. The electrode segment 24 may be positioned along a lateral and/or posterior region of the patient. The electrode segments 22, 24 may be portions of the same lead, or the electrode segments may be portions of different leads. The electrode segments 22, 24 may be positioned subcutaneously at a level that aligns with the heart of the patient for providing a sufficient amount of energy for defibrillation. For example, the electrode segments 22, 24 may be positioned at or below an apex of the heart.

In some embodiments, the lead 20 includes an elongated, common lead coil 70 that includes the electrode segments 22, 24. The electrode segments 22, 24 are portions of the common lead coil 70. In FIG. 1A, the common lead coil 70 extends continuously from a proximal end 23 of the electrode segment 22 to a distal end 25 of the second electrode segment 24. The distal end 25 coincides with the distal tip 64 in FIG. 1A. A proximal end of an electrode segment is the end that is closest to the PG along a path of the lead. A distal end of an electrode segment is the end that is furthest from the PG along the path of the lead. The common lead coil 70 is represented by the electrode segments 22, 24 and an intermediate electrode segment 72 (indicated by dashed lines) that extends between the coils segments 22, 24. More specifically, the common lead coil 70 may be only a single coil electrode that extends continuously (e.g., without interruption) from the proximal end 23 to the distal end 25. In such embodiments, the segments may be indistinguishable.

Alternatively, the electrode segments 22, 24 may be discrete segments that are spaced apart from one another along the lead body 60 or that are positioned along different leads. For example, the electrode segment 22 may be positioned along the anterior of the chest. The lead body 60 may extend from a distal end of the electrode segment 22 to a proximal end of the electrode segment 24. As such, the gap 74 exists between the electrode segments 22, 24 along a length of the lead body 60. A length of the gap 74 may be, for example, at least 10 centimeters (cm). In certain embodiments, the length of the gap 74 may be at least 12 cm, at least 14 cm, or at least 16 cm. In particular embodiments, the length of the gap 74 may be at least 18 cm or at least 20 cm.

The electrode segments 22, 24 (or the common lead coil 70) may be positioned subcutaneously at a level that is suitable for providing a sufficient amount of energy for defibrillation. For example, the electrode segments 22, 24 (or the common lead coil 70) may be positioned subcutaneously at a level that approximately aligns with an apex of a heart of the patient. The electrode segments 22, 24 may be positioned at or below the apex of the heart. For example, the electrode segments 22, 24 (or the common lead coil 70) may be positioned along an intercostal gap between the seventh and eighth ribs of the patient or along an intercostal gap between the sixth and seventh ribs of the patient. It is contemplated, however, that the electrode segments 22, 24 (or the common lead coil 70) may be positioned at other levels with respect to the heart.

Optionally, the electrode segments 22, 24 and the PG electrode 19 (or the housing 18) may be configured to perform sensing (along one or more sensing vectors) and to deliver various types of therapy. The lead 20 is positioned such that the electrode segments 22 and 24 are positioned proximate to (but outside of) various regions or chambers of the heart. In the example of FIG. 1A, the S-IMD 14 is positioned above the heart, while the electrode segment 22 is positioned at a level that is approximately equal to the apex. The electrode segment 24 may be positioned along a lateral region and/or a posterior of the patient. Optionally, the housing 18 of the S-IMD 14 may include one or more electrically separate electrodes, where one combination of electrodes cooperates cooperate to perform sensing and the same or a different combination of electrodes cooperates to deliver therapy.

Figure 1B:
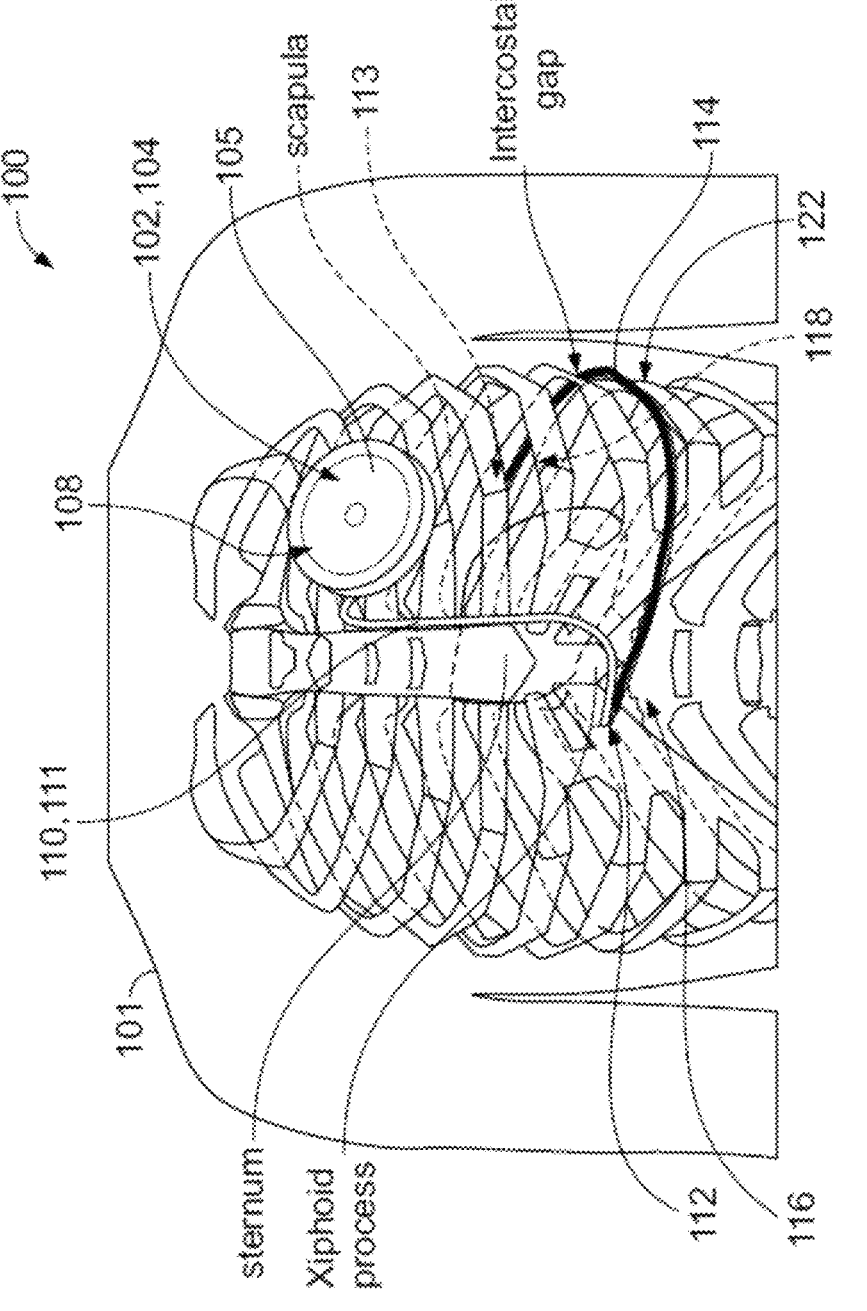
FIG. 1B illustrates one configuration of an implantable medical system in accordance with embodiments herein.

FIG. 1B illustrates one configuration of an implantable medical system 100 in accordance with an embodiment.

FIG. 1B also illustrates the patient's torso and, particularly, the rib cage and the heart. The implantable medical system 100 includes an S-IMD 102 having a pulse generator 104 positioned within a pocket 108 of a pectoral region of a patient 101. The pocket 108 may be a subcutaneous pocket positioned below subcutaneous tissue but above muscle tissue. In alternative embodiments, the pocket may be submuscular (e.g., beneath the pectoral muscle).

The pulse generator 104 includes a housing and/or electrode 105 of the pulse generator 104. In the illustrated embodiment, a single lead 110 is coupled to the pulse generator 104 within the pocket 108. The lead 110 includes a lead body 111 and an elongated lead coil 114. As shown, the lead 110 extends from the pocket 108 in the pectoral region and extra-thoracically along the sternum (e.g., over the sternum or parasternally within one to three centimeters from the sternum). A proximal end 112 of the elongated lead coil 114 is located proximate to the xiphoid process. As shown, the proximal end 112 is positioned along the anterior of the chest on a right side of the sternum. Thus, in some embodiments, the lead 110 may cross over a mid-sternal line that extends through a center of the sternum.

The elongated lead coil 114 has an active length that is measured between the proximal end 112 and a distal end 113. The active length represents a length of the electrode (e.g., a coil electrode) along the lead. As shown, the elongated lead coil 114 extends from proximate to the xiphoid process, along the anterior and side of the patient within an intercostal gap, and along the posterior of the patient toward the spine. As such, the elongated lead coil 114 may wrap about the chest or torso of the patient. The distal end 113 may be positioned proximate to a scapula of the patient. For example, the distal end 113 may be positioned within the intercostal gap and proximate to the tip or the inferior angle of the scapula. The distal end 113 may be positioned between a midaxillary line and a posterior axillary line of the patient. The midaxillary line is a coronal line extending along a surface of the body passing through an apex of the axilla. The posterior axillary line is a coronal line extending parallel to the midaxillary line and through the posterior axillary skinfold. In some instances, the distal end 113 may be positioned beyond the posterior axillary line of the patient.

The elongated lead coil 114 may be characterized as having a first electrode segment 116 that includes the proximal end 112, and a second electrode segment 118 that includes the distal end 113. For embodiments in which the elongated lead coil 114 extends substantially continuously from the proximal end 112 to the distal end 113, the elongated lead coil 114 may also have an intermediate electrode segment 122 that extends between the first and second electrode segments 116, 118. The first and second electrode segments 116, 118 and the intermediate segment 122 may be indistinguishable such that the elongated coil 114 extends continuously between the proximal end 112 and the distal end 113. Alternatively, the intermediate electrode segment 122 may be discrete with respect to the first and second electrode segments 116, 118 such that gaps or spacings exist between the electrode segments.

In some embodiments, at least one of the electrode segments 116, 118, 122 is a shock coil and at least one of the electrode segments 116, 118, 122 is a sensing electrode. In other embodiments, each of the first electrode segment 116, the second electrode segment 118, and the intermediate segment 122 is a shock coil. In certain embodiments, the first electrode segment 116, the second electrode segment 118, and/or the intermediate segment 122 are electrically common (have same polarity) with one another.

In the illustrated embodiment, the elongated coil 114 extends through the same intercostal gap from the side or lateral portion of the patient to the posterior of the patient. Optionally, the elongated coil 114 may extend over a rib to move from one intercostal gap to another intercostal gap. In some cases, one or more portions of the elongated coil 114 may be positioned higher, such as even or level with a mid-plane extending through the heart.

In some embodiments, the active length of the elongated lead coil 114 is at least thirty (30) centimeters (cm). In particular embodiments, the active length of the elongated lead coil 114 may be at least thirty-five (35) cm. In more particular embodiments, the active length of the elongated lead coil 114 may be at least forty (40) cm. The active length of the elongated lead coil 114 may be at most fifty (50) cm or at most forty-five (45) cm. Accordingly, embodiments may include a lead having a single elongated coil (e.g., coil electrode) that has an active length of at least 30 cm extending from anterior to posterior of the patient while wrapping about a side (or lateral portion) of the chest.

Figure 1C:
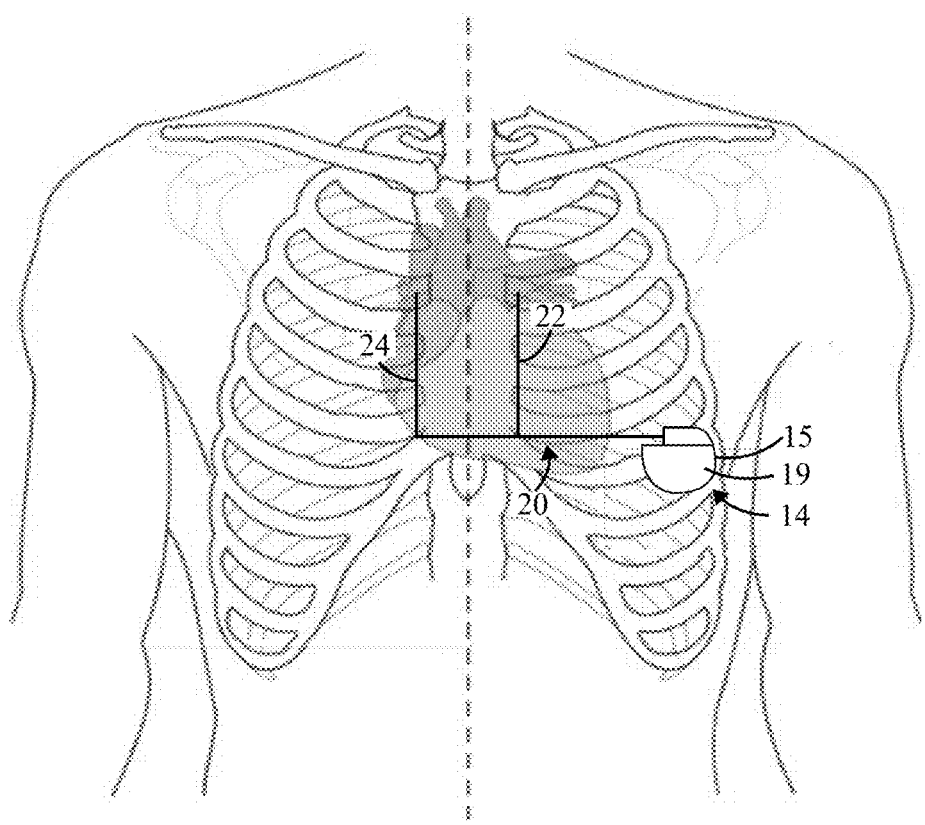
FIG. 1C illustrates a graphical representation of an S-IMD medical system that is configured to apply therapy to a heart in accordance with embodiments herein.

FIG. 1C illustrates a graphical representation of an S-IMD medical system that is configured to apply therapy to a heart. FIG. 1C illustrates a torso of a patient to show the rib cage and a general outline of the heart and greater vessels. In particular embodiments, the system may apply high voltage defibrillation shocks. The system includes an S-IMD 14 that is configured to be implanted in a subcutaneous area exterior to the heart. The system includes only the S-IMD 14 and is entirely or fully subcutaneous. As shown in FIG. 1C, the S-IMD 14 is positioned within a lateral region, such as along the left side of the rib cage under the left arm. The S-IMD 14 may be positioned relative to a vertical direction substantially aligned with the apex of the heart. The S-IMD 14 is configured to deliver defibrillation therapy. The system does not require insertion of a transvenous lead. It is contemplated, however, that system may include other components. For example, alternative embodiments may include a transvenous lead or a leadless electrode in addition to the structures in FIG. 1C.

The lead 20 includes at least two electrodes 22, 24 that are used for providing electrical shock for defibrillation. Optionally, the lead 20 may include one or more sensing electrodes. The pulse generator 15 may be implanted subcutaneously and at least a portion of the lead 20 may be implanted subcutaneously. In particular embodiments, the S-IMD 14 is an entirely or fully subcutaneous S-IMD. The pulse generator 15 may be positioned at a lateral position or below an apex of the heart. The first electrode 22 may be positioned along a left side of the anterior region of the chest adjacent to the sternum. The second electrode 24 may be positioned along a right side of the anterior region of the chest adjacent to the sternum. For example, the electrodes 22, 24 may be spaced equal distances from a midline extending vertically through a patient along a center of the sternum. Optionally, one of the electrodes 22, 24 may be positioned laterally closer to the sternum and midline, while the other of the electrodes 22, 24 is positioned laterally further away from the sternum and midline. The electrodes 22, 24 may be positioned subcutaneously to extend vertically along a region adjacent opposite sides of the sternum that aligns with the heart of the patient for providing a sufficient amount of energy for defibrillation.

Figure 2A:
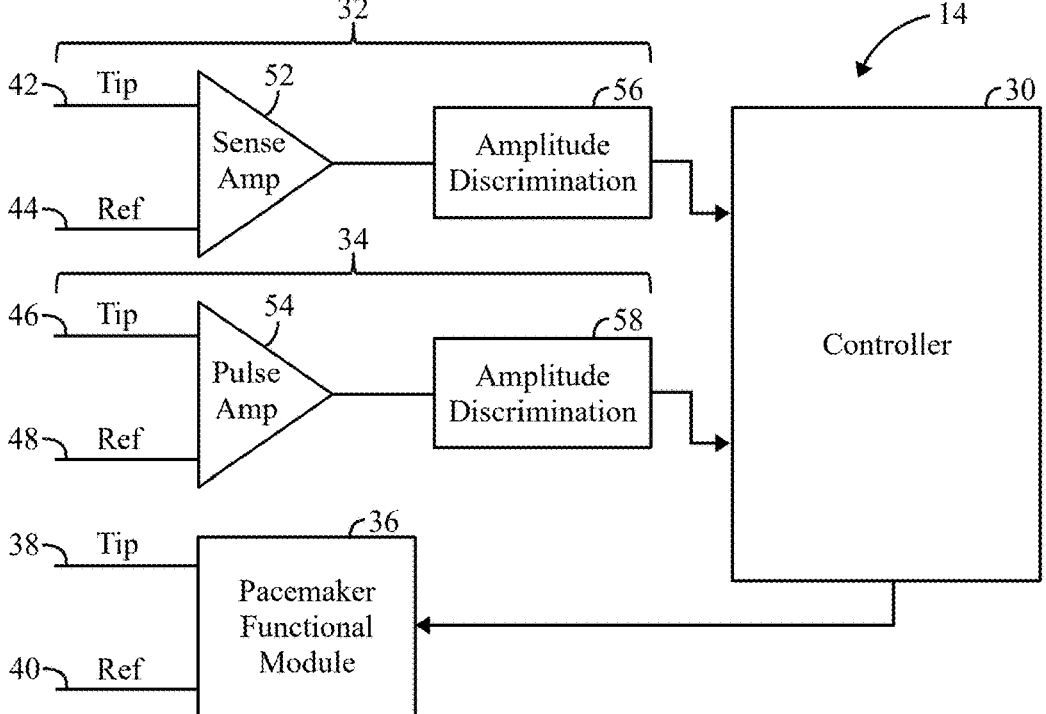
FIG. 2A illustrates a simple block diagram of at least a portion of the circuitry within the S-IMD in accordance with embodiments herein.

FIG. 2A illustrates a simple block diagram of at least a portion of the circuitry within the S-IMD 14. The S-IMD 14 includes a controller 30 that may be coupled to cardiac sensing circuitry 32 and pulse sensing circuitry 34. The controller 30 also utilizes or communicates with various other electronic components, firmware, software, and the like that generally perform sensing and pacing functions (as generally denoted by a pacemaker functional block 36). While the examples herein are provided for pacing and defibrillation functions, the S-IMD could be programmed to perform anti-tachycardia pacing, cardiac rhythm therapy, and the like. The cardiac sensing circuitry 32 is configured to detect cardiac events. The pulse sensing circuitry 34 is configured to detect event markers.

The controller 30 is configured to analyze incoming paced cardiac events (as sensed over the cardiac sensing circuitry 32). Based on this analysis, the controller 30 in the S-IMD 14 may perform various pacemaker related actions, such as setting or ending timers, recording data, delivery of therapy, and the like. The controller 30 of the S-IMD 14 may also perform various cardioversion/defibrillation related functions. In an example, outputs 38 and 40 represent output terminals that are coupled through a switching circuit (in the functional module 36) to corresponding electrodes on the housing of the S-IMD 14. Alternatively, the outputs 38 and 40 may be coupled to respective electrodes on along the lead 20 (FIG. 1C).

Inputs 42-48 are provided to the cardiac and pulse sensing circuitry 32 and 34. By way of example, with reference to S-IMD 14, inputs 42 and 44 may be coupled to sensing electrodes that supply sensed signals to a sensing amplifier 52. Inputs 46 and 48 may be coupled to the same or different sensing electrodes to provide sensed signals to a pulse amplifier 54. An output of the sensing amplifier 52 is supplied to amplitude discriminator 56, while an output of the pulse amplifier 54 is supplied to amplitude discriminator 58. Outputs of the amplitude discriminators 56 and 58 are then provided to the controller 30 for subsequent analysis and appropriate actions. The inputs 42 and 44 may be coupled to various combinations of the electrodes 22, 24 or the PG electrode 19.

Figure 2B:
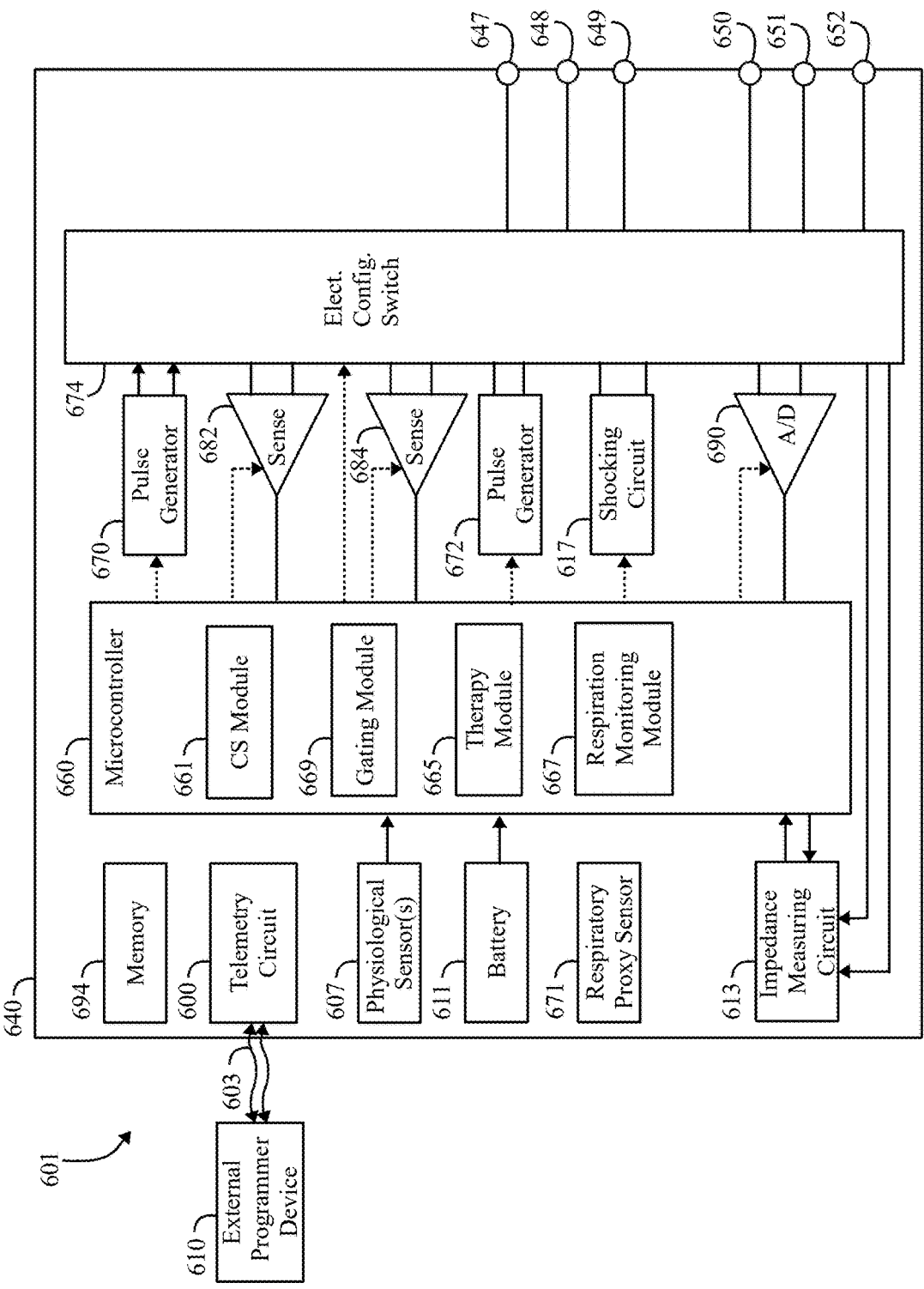
FIG. 2B illustrates a block diagram of an S-IMD in accordance with embodiments herein.

FIG. 2B illustrates a block diagram of an S-IMD. The S-IMD 601 is capable of performing stimulation therapy, including cardioversion, defibrillation, and pacing stimulation. The S-IMD 601 is hereinafter referred to as the device 610. While a particular multi-element device is shown, this is for illustration purposes only. It is understood that the appropriate circuitry could be duplicated, eliminated or disabled in any desired combination to provide a device capable of monitoring impedance and/or cardiac signals, and/or treating the appropriate chamber(s) with cardioversion, defibrillation and pacing stimulation.

The housing 640 for the device 610 is often referred to as the "canister," "can," "case," or "case electrode" and may be programmably selected to act as the shock electrode and/or as a return electrode for some or all sensing modes. The housing 640 may further be used as a return electrode alone or in combination with one or more other electrodes. The housing 640 further includes a connector (not shown) having a plurality of terminals 647-652. To achieve sensing, pacing, and shocking in connection with desired chambers of the heart, the terminals 647-652 are selectively connected to corresponding combinations of electrodes.

The device 610 includes a programmable microcontroller 660 that controls the various modes of sensing and stimulation therapy. The microcontroller 660 includes a microprocessor, or equivalent control circuitry, designed specifically for controlling sensing impedance derivation and the delivery of stimulation therapy and may further include RAM or ROM memory, logic and timing circuitry, state machine circuitry, and I/O circuitry. The microcontroller 660 includes the ability to process or monitor input signals (data) as controlled by a program code stored in memory. The details of the design and operation of the microcontroller 660 are not critical to the present invention. Rather, any suitable microcontroller 660 may be used.

The microcontroller 660 includes inputs that are configured to collect cardiac signals associated with electrical or mechanical behavior of a heart over at least one cardiac cycle. The cardiac signals may be from the cardiac sensing circuit 682 and representative of electrical behavior of the heart. The circuit 682 may provide separate, combined, composite or difference signals to the microcontroller 660 representative of the sensed signals from the electrodes. Optionally, the cardiac signals may be the output of the A/D circuit 690 that are representative of electrical behavior of the heart. The cardiac signals may be the output of the physiological sensor 607 that are representative of mechanical behavior.

A respiration proxy sensor 671 is configured to obtain a respiration proxy signal indicative of respiration, the respiration proxy signal varying over a respiratory cycle. For example, the respiration proxy sensor may take impedance measurements that can be used to detect the respiratory cycle. Large-field vectors for measuring current and voltage can be configured with a respiratory-frequency passband filter to track respiratory cycles. Further, during normal rhythm, the modulation of cardiogenic vectors in near-field (e.g., RV bipolar or RV-LV quadpolar—representing cardiac contractility and/or heart wall motion) or far-field (e.g., RA to case bipolar—representing blood ejection through the great vessels and/or venous return) may also be used to get baseline respiratory rates. In one embodiment, underlying cardiogenic signals associated with respiratory modulation of contractility or stroke volume may be measured. In another embodiment, thoracic impedance may be directly measured.

Additionally or alternatively, the respiratory proxy sensor may utilize a "wideband" electrogram channel to estimate the respiratory cycle of a patient. This may be the same channel as is used for PVC, template matching, and other discrimination features. In one embodiment, baseline wander, or low frequency content of the electrogram signal, is measured. In an embodiment, modulation of R wave peak amplitude or integral and modulation of T wave peak amplitude integral, under stable rhythm is measured. In an embodiment, modulation of R-R intervals by respiratory sinus arrhythmia (RSA) may be measured as a surrogate for the respiratory cycle.

Additionally or alternatively, the respiratory proxy sensor may utilize a 3D MEMS accelerometer to estimate a patient's respiratory cycle. In a wideband mode the accelerometer may detect low frequency motion corresponding with respiration. Raw accelerations can capture actual chest wall movement, the expansion and contraction of breathing. Higher frequencies may capture breath sounds, particularly in patients who may have some degree of congestion or other cardio-respiratory comorbidities. In an embodiment, detection of heart sounds may be used to estimate respiration cycles. In an embodiment using an accelerometer, actual respiratory motion or breath sounds may produce detectable signals.

The microcontroller 660 includes a cardiac signal (CS) module 661 and a therapy module 665 (among other things). The CS module 661 is configured to analyze cardiac signals, including detecting and declaring shockable arrhythmias, such as ventricular fibrillation episodes. The therapy module

665 is configured to deliver therapy in the form of a shock responsive to direction from the microprocessor. The therapy module 665 is further configured to adjust a therapy configuration based on, among other things, the cardiac signals and based on the respiratory proxy signals.

The microcontroller 660 further includes a respiration monitoring module 667 and a gating module 669 that are defined by program instructions, that when executed, are configured to perform the operations described herein. Among other things, the respiration monitoring module 667 obtains a respiration proxy signal indicative of respiration, wherein the respiration proxy signal varies over a respiration cycle. The respiration monitoring module 667 tracks a respiration state related (RSR) characteristic from the respiration proxy signal. The gating module 669 gates delivery of a high voltage (HV) shock based on occurrence of a respiration-gated (RG) trigger in connection with the RSR characteristic. The RG trigger corresponds to a point in time when the RSR characteristic indicates a select state within the respiration cycle. The microcontroller 660 directs delivery of the HV shock along a shocking vector between shocking electrodes based on the RG trigger to time delivering of the HV shock to occur during the select state within the respiration cycle.

For example, the microcontroller 660 directs the respiration monitoring module 667 to track an RSR characteristic, wherein the RSR characteristic comprises a slope of the respiration proxy signal. Optionally, the RG trigger occurs when the slope transitions from a negative value to a positive value, the slope transition corresponding to a point in the respiration proxy signal indicative of peak expiration. The microcontroller 660 directs the gating module 669 to gate delivery of a high voltage (HV) shock based on occurrence of the RG trigger.

In another example, the microcontroller 660 directs the respiration monitoring module 667 to track an RSR characteristic, wherein the RSR characteristic represents a peak to peak amplitude range of one or more breaths. Optionally, the RG trigger occurs when a current level of the respiration proxy signal falls a select amplitude drop below an amplitude corresponding to peak inspiration, wherein the select amplitude drop corresponds to a percentage of the peak to peak amplitude range of one or more breaths. The microcontroller 660 directs the gating module 669 to gate delivery of a high voltage (HV) shock based on occurrence of the RG trigger.

In another example, the microcontroller 660 directs the respiration monitoring module 667 to track an RSR characteristic, wherein the RSR characteristic represents a minimum amplitude of the respiration proxy signal. Optionally, the RG trigger occurs when a current level of the respiration proxy signal falls to a select window surrounding the minimum amplitude of the respiration proxy signal corresponding to peak expiration. The microcontroller 660 directs the gating module 669 to gate delivery of a high voltage (HV) shock based on occurrence of the RG trigger.

In another example, the microcontroller 660 directs the respiration monitoring module 667 to track an RSR characteristic, wherein the RSR characteristic represents a respiratory period. Optionally, the RG trigger occurs when a time period, that corresponds to the respiratory period, elapses following a peak expiration of a most recent breath. The microcontroller 660 directs the gating module 669 to gate delivery of a high voltage (HV) shock based on occurrence of the RG trigger.

In another example, the microcontroller 660 directs the respiration monitoring module 667 to track an RSR characteristic, wherein the RSR characteristic represents a respiratory period. Optionally, the RG trigger occurs when a time period, corresponding to a select amount of the respiratory period, elapses following a peak inspiration of a most recent breath. The microcontroller 660 directs the gating module 669 to gate delivery of a high voltage (HV) shock based on occurrence of the RG trigger.

In another example, the microcontroller 660 directs the respiration monitoring module 667 to measure the signal indicative of respiration during normal sinus rhythm to obtain at least one of a baseline peak to peak (P-P) range or a baseline respiratory period and to define a time out value based on the respiratory period. Optionally, the microcontroller 660 directs the gating module 669 to gate delivery of an HV shock, wherein the gating further comprises setting a timer based on the time out value, initiating the timer in connection with the declaring the shockable arrhythmia (e.g., fibrillation episode), the delivering comprising initiating delivery of the HV shock in response to expiration of the timer independent of whether the RG trigger occurs.

In another example, the microcontroller 660 directs the respiration monitoring module 667 to obtain at least one of thoracic impedance measurements or cardiogenic impedance measurements indicative of a respiratory cycle and obtain the at least one of the estimated respiration depth or respiration phase from the respiratory cycle.

In another example, the microcontroller 660 directs the respiration monitoring module 667 to obtain wideband electrogram signals, filter the electrogram signals for a low frequency content indicative of a respiratory cycle, and obtain the at least one of the estimated respiration depth or respiration phase from the respiratory cycle.

In another example, the microcontroller 660 directs the respiration monitoring module 667 to obtain an accelerometer signal from an accelerometer, filter the accelerometer signal to obtain a low frequency motion component indicative of a respiratory cycle, and obtain the at least one of the estimated respiration depth or respiration phase from the respiratory cycle.

The microcontroller 660 further controls a shocking circuit 617 by way of a control signal. The shocking circuit 617 generates stimulating pulses of low (up to 0.5 Joules), moderate (0.5-10 Joules), or high energy (11 to 50 Joules), as controlled by the microcontroller 660. The stimulating pulses may be applied to the patient's heart through at least two shocking electrodes.

One or more pulse generators 670 and 672 generate various types of therapy, such as pacing and ATP stimulation pulses for delivery by desired electrodes. The electrode configuration switch 674 (also referred to as a switch bank) controls which terminals 647-652 are connected to the pulse generators 670, 672, thereby controlling which electrodes receive a therapy. The pulse generators, 670 and 672, may include dedicated, independent pulse generators, multiplexed pulse generators, shared pulse generators or a single common pulse generator. The pulse generators 670 and 672 are controlled by the microcontroller 660 via appropriate control signals to trigger or inhibit stimulation pulses. The microcontroller 660 further includes timing control circuitry which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, PVARP intervals, noise detection windows, evoked response windows, alert intervals, marker channel timing, etc.

An electrode configuration switch 674 connects the sensing electronics to the desired terminals 647-652 of corresponding sensing electrodes. For example, a portion of the terminals may be coupled to electrodes configured to define a sensing and/or shocking vector that passes through the left ventricle. The switch 674 may connect terminals to the event marker sensing circuit 684 (which corresponds to the event marker sensing channel) and the microcontroller. The circuit 684 may amplify, filter, digitize and/or otherwise process the sensed signals from the select electrodes.

The switch 674 also connects various combinations of the electrodes to an impedance measuring circuit 613. The impedance measuring circuit 613 includes inputs to collect multiple measured impedances between corresponding multiple combinations of electrodes. For example, the impedance measuring circuit 613 may collect a measured impedance for each or a subset of the active sensing vectors. Optionally, the impedance measuring circuit 613 may measure respiration or minute ventilation; measure thoracic impedance for determining shock thresholds; detect when the device has been implanted; measure stroke volume; and detect the opening of heart valves, etc.

The switch bank 674 includes a plurality of switches for connecting the desired electrodes to the appropriate I/O circuits, thereby providing complete electrode programmability. The switch 674, in response to a control signal from the microcontroller 660, determines the polarity of the stimulation pulses (e.g., unipolar, bipolar, co-bipolar, etc.) by selectively closing the appropriate combination of switches (not specifically shown). The outputs of the cardiac signal and event marker sensing circuits 682 and 684 are connected to the microcontroller 660 which, in turn, is able to trigger or inhibit the pulse generators 670 and 672, respectively. The sensing circuits 682 and 684, in turn, receive control signals from the microcontroller 660 for purposes of controlling the gain, threshold, the polarization charge removal circuitry (not shown), and the timing of any blocking circuitry (not shown).

Cardiac signals are also applied to the inputs of an analog-to-digital (A/D) data acquisition system 690. The data acquisition system 690 is configured to acquire cardiac signals, convert the raw analog data into a digital signal, and store the digital signals for later processing and/or telemetric transmission to an external device. The data acquisition system 690 samples cardiac signals across any pair of desired electrodes. The data acquisition system 690 may be coupled to the microcontroller 660, or other detection circuitry, for detecting an evoked response from the heart in response to an applied stimulus, thereby aiding in the detection of "capture." Capture occurs when an electrical stimulus applied to the heart is of sufficient energy to depolarize the cardiac tissue, thereby causing the heart muscle to contract.

The microcontroller 660 is further coupled to a memory 694 by a suitable data/address bus. The memory 694 stores programmable operating, impedance measurements, impedance derivation and therapy-related parameters used by the microcontroller 660. The operating and therapy-related parameters define, for example, pacing pulse amplitude, pulse duration, electrode polarity, rate, sensitivity, automatic features, arrhythmia detection criteria, and the amplitude, wave shape and vector of each stimulating pulse to be delivered to the patient's heart within each respective tier of therapy.

The operating and therapy-related parameters may be non-invasively programmed into the memory 694 through a telemetry circuit 600 in telemetric communication with the external device, such as a programmer, trans-telephonic transceiver, or a diagnostic system analyzer. The telemetry circuit 600 is activated by the microcontroller 660 by a control signal. The telemetry circuit 600 advantageously allows data and status information relating to the operation of the device (as contained in the microcontroller 660 or memory 694) to be sent to an external device 610 through an established communication link 603.

The device 610 may include a physiological sensor 607 to adjust pacing stimulation rate according to the exercise state of the patient. The physiological sensor 607 may further be used to detect changes in cardiac output, changes in the physiological condition of the heart, or diurnal changes in activity (e.g., detecting sleep and wake states). The battery 611 provides operating power to all of the circuits.

Figure 3:
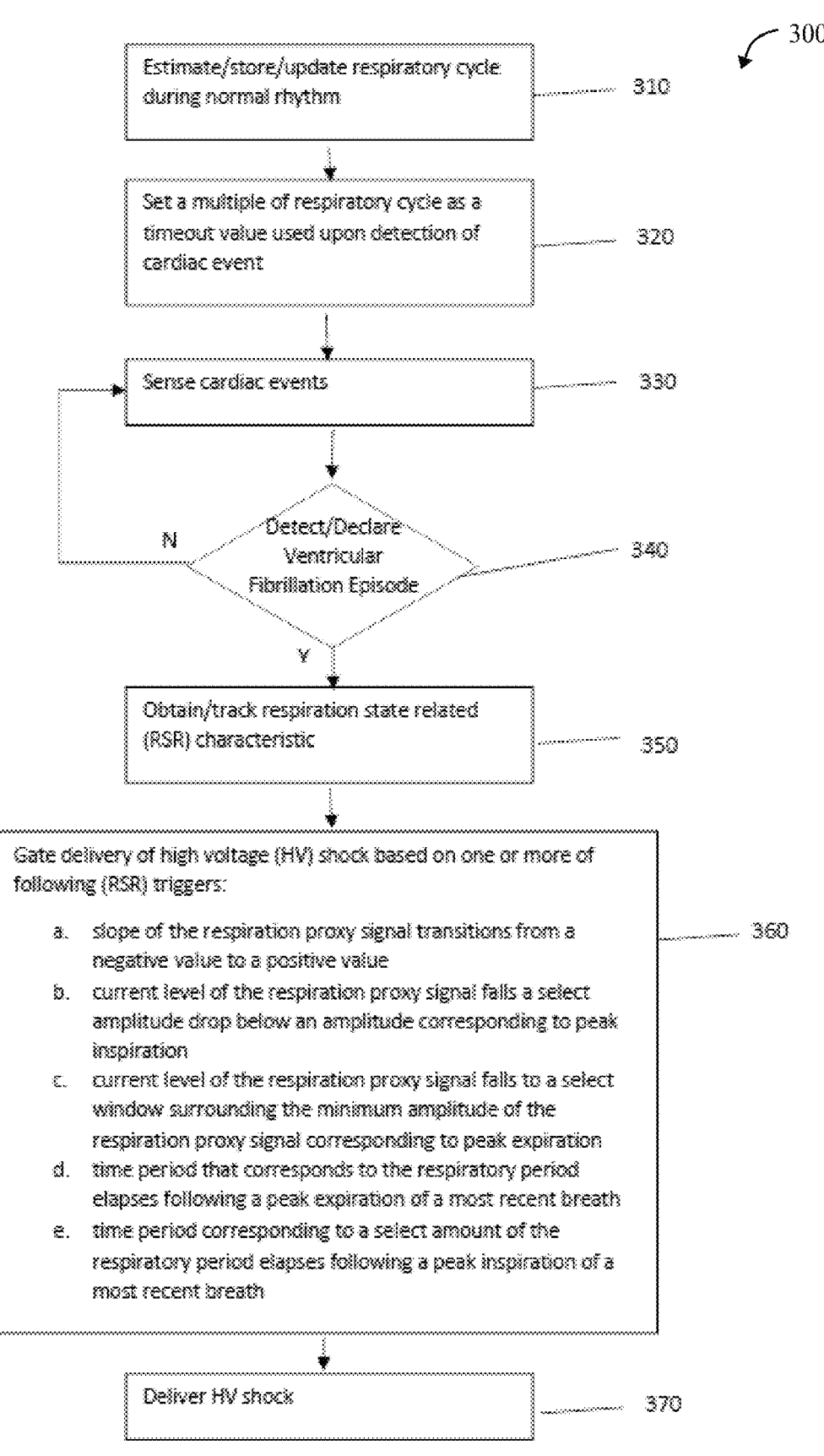
FIG. 3 illustrates a flow chart of a method for managing delivery of a respiratory gated defibrillation shock from an S-IMD in accordance with embodiments herein.

FIG. 3 illustrates a flow chart of a method for managing delivery of a respiratory gated defibrillation shock from an S-IMD in accordance with an embodiment. The method 300 includes estimating, storing, and updating a patient's respiratory cycle.

At 310, one or more processors estimate the respiratory cycle in various ways. Once the respiratory cycle has been estimated, the processor may be configured to save respiratory cycle data to memory. The memory may store the respiratory data for a predetermined period of time. The processor may also be configured to update respiratory cycle data according to predetermined parameters. Non-limiting examples of parameters include a state condition in which a patient is at rest, a patient is active and the like. For example, the processors may update the respiratory cycle data when an accelerometer or other sensor determines that a patient is at rest. Additionally or alternatively, the processors may update the respiratory cycle data when an accelerometer or other sensor determines that a patient is undergoing activity. The processor may be configured to periodically estimate, store, and update respiratory cycle data. Alternatively, the processor may be configured to continuously, estimate, store, and update respiratory cycle data.

At 320, the one or more processors may set a multiple of the respiratory cycle as a timeout value. As explained herein, the timeout value is used upon detection of a cardiac event of interest (e.g., a ventricular fibrillation event). The timeout value may serve as an outer limit for a period of time permitted to lapse, following a declaration that a ventricular fibrillation event has started, before delivering an HV shock (regardless of the state of the respiratory cycle at the time the timeout occurs). The timeout value may represent a value that corresponds to the interval of time between detection of a shockable cardiac event and delivery of the HV shock. The timeout value may be a multiple of the respiratory cycle. For example, a timeout value of 1.63 times the respiratory cycle or 1.63× may be selected as the value utilized upon detection of a cardiac event, the value at which a patient's heart may require an HV shock. The cardiac event may be tachyarrhythmia or another serious cardiac event.

At 330, the one or more processors sense cardiac activity and analyzes the cardiac activity to determine whether a cardiac event-of-interest has occurred. In response to determining that the cardiac event-of-interest has occurred, a therapy may be applied. For example, the pulse generator may sense subcutaneous signals (e.g., subcutaneous ECG signals) and a cardiac rhythm using a combination of the electrodes. The pulse generator may process the cardiac signals (e.g., filter and/or amplify) and analyze the cardiac activity to determine whether an event that requires therapy is occurring. If the pulse generator determines that a cardiac event-of-interest is occurring, such as ventricular fibrillation, ventricular tachycardia, or other arrhythmia, the pulse generator may apply therapy (e.g., electrical shock) to the heart using a combination of the electrodes. As mentioned above, the timeout value may be the threshold for sensing cardiac events. The method will continue to monitor for cardiac events.

At 340, the one or more processors continue to provide monitoring of the patient's cardiac condition. If a shockable arrhythmia (e.g., ventricular fibrillation episode) is not detected, the one or more processors continue to provide monitoring of the patient's cardiac condition. If the one or more processors detect a cardiac event, the timeout value is attained, and a shockable arrhythmia (e.g., ventricular fibrillation episode) is detected at 340.

At 350 the one or more processors obtain a respiration proxy signal indicative of respiration. The respiration proxy signal may vary over a respiration cycle. In an embodiment, the processor obtains at least one of thoracic impedance measurements or cardiogenic impedance measurements indicative of a respiratory cycle and obtains at least one of the estimated respiration depth or respiration phase from the respiratory cycle. In an embodiment, the processor obtains wideband electrogram signals, filters the electrogram signals for a low frequency content indicative of a respiratory cycle, and obtains the at least one of the estimated respiration depth or respiration phase from the respiratory cycle. In an embodiment, the processor obtains an accelerometer signal from an accelerometer, filters the accelerometer signal to obtain a low frequency motion component indicative of a respiratory cycle, and obtains the at least one of the estimated respiration depth or respiration phase from the respiratory cycle. The method further provides for the tracking of a respiration state related (RSR) characteristic from the respiration proxy signal. For example, RSR characteristics may include the depth or phase of respiration, a slope of the respiration proxy signal, peak-to-peak amplitude range of one or more breaths, a minimum amplitude of the respiration proxy signal, and/or a respiration period. After the processor has obtained and tracked the RSR characteristic, the method then proceeds to 360.

At 360 the one or more processors gate delivery of an HV shock based on the occurrence of one or more RG triggers in connection with corresponding RSR characteristics. The RG trigger may correspond to a point in time when the corresponding RSR characteristic indicates a select state within the respiration cycle. In an embodiment, the RSR characteristic includes a slope of the respiration proxy signal and an RG trigger may occur when the slope transitions from a negative value to a positive value, the slope transition corresponding to a point in the respiration proxy signal indicative of peak expiration. In an embodiment, the RSR characteristic represents a peak to peak amplitude range of one or more breaths and the RG trigger occurs when a current level of the respiration proxy signal falls a select amplitude drop below an amplitude corresponding to peak inspiration. By way of example, the select amplitude drop may correspond to a percentage of the peak to peak amplitude range of one or more breaths. In an embodiment, the RSR characteristic represents a minimum amplitude of the respiration proxy signal and the RG trigger occurs when a current level of the respiration proxy signal falls to a select window surrounding the minimum amplitude of the respiration proxy signal corresponding to peak expiration. In an embodiment, the RSR characteristic represents a respiratory period and the RG trigger occurs when a time period, that corresponds to the respiratory period, elapses following a peak expiration of a most recent breath. In an embodiment, the RSR characteristic represents a respiratory period and the RG trigger occurs when a time period, corresponding to a select amount of the respiratory period, elapses following a peak inspiration of a most recent breath.

FIGS. 4A-4E illustrate a collection of graphical representations of a respiratory proxy signal analyzed in accordance with embodiments herein. FIGS. 4A-4E illustrate a horizontal axis corresponding to time associated with at least one respiratory cycle, and a vertical axis corresponding to a point in an instantaneous point in a respiratory cycle fluctuating between the peak expiration and a peak inspiration, such as similar to a sine wave or other repeating wave.

Figure 4A:
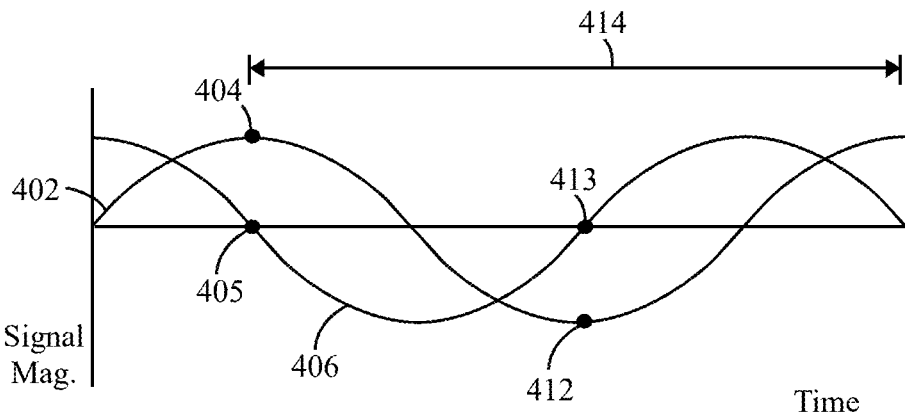
FIG. 4A illustrates the respiratory proxy signal fluctuates between a peak inspiration and peak expiration over a respiratory period in accordance with embodiments herein.

In FIG. 4A, the respiratory proxy signal 402 fluctuates between a peak inspiration 404 and peak expiration 412 over a respiratory period 414. The respiratory proxy signal 402 may be sensed by one or more of the sensors described herein. As described in connection with FIG. 3, the one or more processors track of one or more respiration state related (RSR) characteristics from the respiration proxy signal 402. As noted herein, the RSR characteristic may represent a slope of the respiration proxy signal 402. In connection there with, the one or more processors continuously or at discrete points, determine a slope 406 of the respiratory proxy signal 402. In FIG. 4A the respiration proxy signal 402 generally represents a sine wave, and therefore, the one or more processors would identify the slope 406 to generally represent a cosine, such as having a 90-degree phase shift leading the sine wave. When the respiration proxy signal 402 reaches a peak inspiration 404, the slope 406 exhibits a transition from a positive slope to a negative slope at 405. When the respiration proxy signal 402 reaches a peak expiration at 412, the slope 406 exhibits a transition from a negative slope to a positive slope at 413. The one or more processors monitor the slope, as the RSR characteristic, and identify an RG trigger when the slope transitions from a negative slope to a positive slope at 413.

Figure 4B:
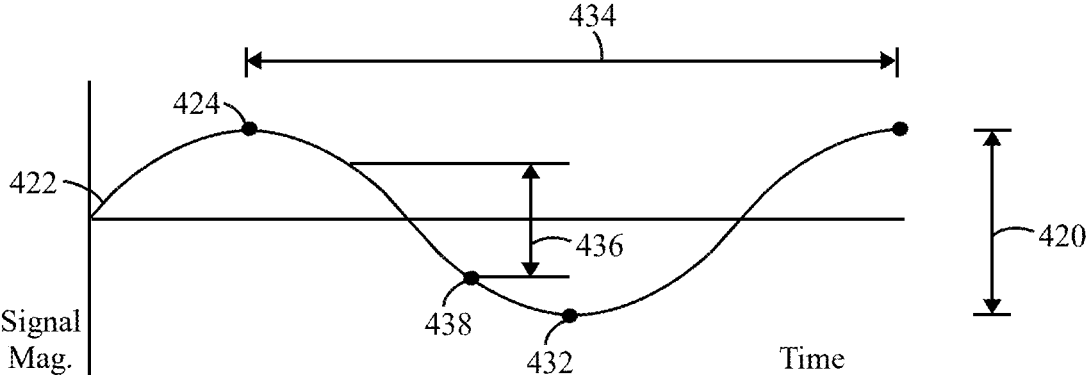
FIG. 4B illustrates the respiratory proxy signal to fluctuate between a peak inspiration and peak expiration over a respiratory period in accordance with embodiments herein.

Additionally or alternatively, the one or more processors may track an RSR characteristic corresponding to a peak to peak amplitude range. To further illustrate this point, reference is made to FIG. 4B. FIG. 4B illustrates the respiratory proxy signal 422 to fluctuate between a peak inspiration 424 and peak expiration 432 over a respiratory period 434. In accordance therewith, during one or more prior respiratory cycles, the one or more processors determine a peak to peak amplitude range 420 of one or more prior breaths. The one or more processors monitor a current level/amplitude of the respiratory proxy signal 422 and compares the amplitude to a select amplitude drop 436 below an amplitude 438 of a most recent peak inspiration 424. When the current amplitude of the respiratory proxy signal 422 drops below the select amplitude drop 436, the one or more processors declare the RG trigger to have occurred. In the present example, the amplitude drop 436 is defined to correspond to a predetermined percentage of the peak to peak amplitude range 420 (e.g., 80%).

Figure 4C:
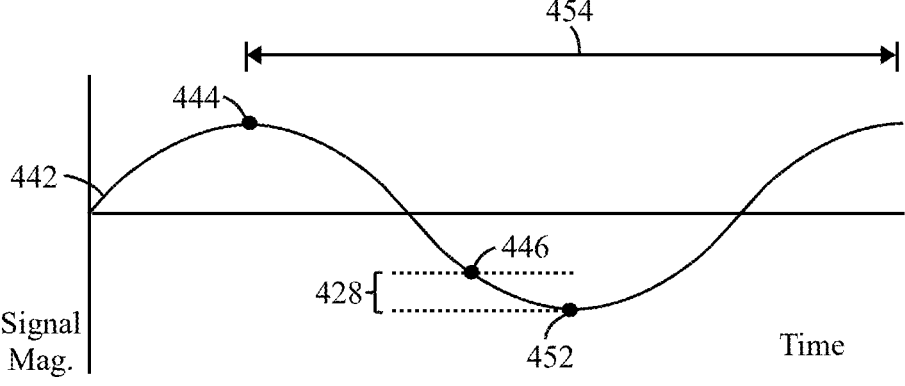
FIG. 4C illustrates the respiratory proxy signal fluctuating between a peak inspiration and peak expiration over a respiratory period in accordance with embodiments herein.

Additionally or alternatively, the one or more processors may track an RSR characteristic corresponding to a minimum amplitude range. To further illustrate this point, reference is made to FIG. 4C. FIG. 4C illustrates the respiratory proxy signal 442 fluctuating between a peak inspiration 444 and peak expiration 452 over a respiratory period 454. In accordance therewith, during one or more prior respiratory cycles, the one or more processors determine a minimum amplitude 446 of the respiration proxy signal corresponding to one or more prior breaths. The one or more processors monitor a current level/amplitude of the respiratory proxy signal 442 and compares the amplitude to a select window 428 surrounding the minimum amplitude 446 of the respiration proxy signal 442 corresponding to peak expiration 452. When the current amplitude of the respiratory proxy signal 422 drops to or within the select window 428, the one or more processors declare the RG trigger to have occurred.

Figure 4D:
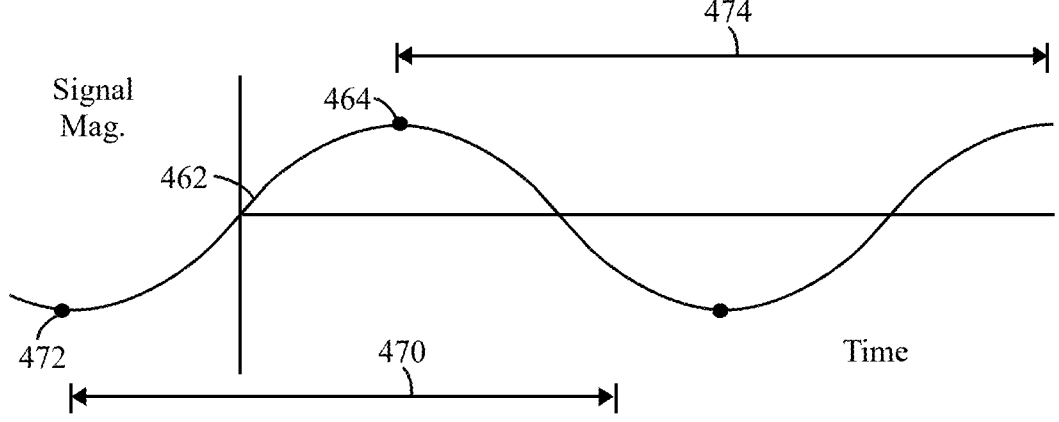
FIG. 4D illustrates the respiratory proxy signal fluctuating between a peak expiration and peak inspiration over a respiratory period in accordance with embodiments herein.

Additionally or alternatively, the one or more processors may track an RSR characteristic corresponding to a respiratory time period. To further illustrate this point, reference is made to FIG. 4D. FIG. 4D illustrates the respiratory proxy signal 462 fluctuating between a peak expiration 472 and peak inspiration 464 over a respiratory period 474. In accordance therewith, during one or more prior respiratory cycles, the one or more processors determine a respiratory time period 470 associated with one or more prior breaths. The one or more processors monitor a current level/amplitude of the respiratory proxy signal 462 and a time period 470 that corresponds to the respiratory period 474. When the time period 470 elapses following a peak expiration 472 of a most recent breath, the one or more processors declare the RG trigger to have occurred. The time period 470 may also be considered a time out period.

Figure 4E:
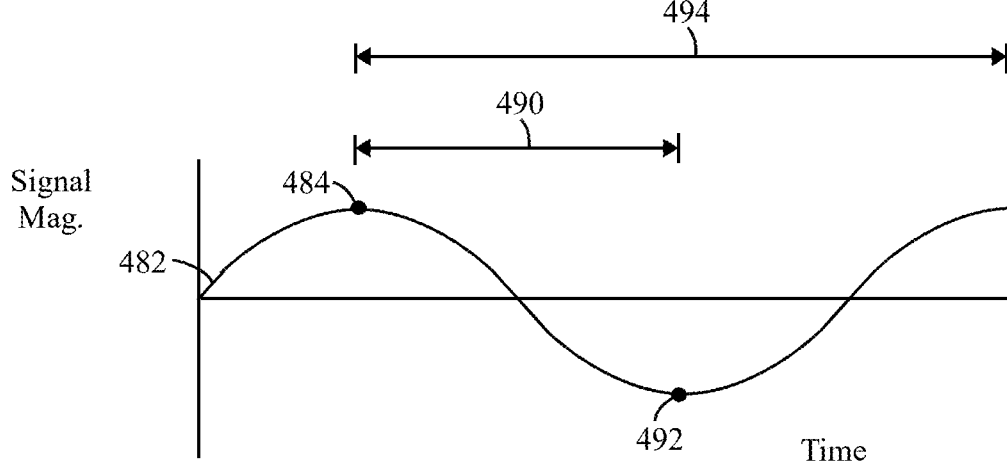
FIG. 4E illustrates the respiratory proxy signal fluctuating between a peak inspiration and peak expiration over a respiratory period in accordance with embodiments herein.

Additionally or alternatively, the one or more processors may track an RSR characteristic corresponding to another respiratory time period. To further illustrate this point, reference is made to FIG. 4E. FIG. 4E illustrates the respiratory proxy signal 482 fluctuating between a peak inspiration 484 and peak expiration 492 over a respiratory period 494. In accordance therewith, during one or more prior respiratory cycles, the one or more processors determine a time period 490 associated with one or more prior breaths. The one or more processors monitor a current level/amplitude of the respiratory proxy signal 482 and a time period 490 that corresponds to the respiratory period 494. When the time period 490 elapses following a peak inspiration 484 of a most recent breath, the one or more processors declare the RG trigger to have occurred. The time period 490 may also be considered a time out period.

Turning back to FIG. 3, at 370, the one or more processors may direct a shocking circuit to deliver the HV shock along a shocking vector between S-IMD electrodes based on the RG trigger to time delivering of the HV shock to occur during the select state within the respiration cycle. The shocking circuit may generate stimulating pulses to be applied to a patient's heart through shocking elements. The processor may also determine and control the amount of energy delivered through the S-IMD electrodes. Further, the processor may determine and control the timing of the stimulating pulses at an interval required to give the stimulated heart an opportunity to recover from the HV shock and receive another shock if necessary. For example, in an embodiment, a patient's respiration may be monitored and measured to determine a signal that represents the patient's respiratory period. The processor may establish a timeout value based on the respiratory period. Upon detection of a cardiac event, the processor may gate the HV shock therapy responsive to one or more RG triggers for timing delivery of the HV shock. If the processor determines that a second defibrillation attempt is necessary, the processor may establish an interval of one pulse per minute and direct the shocking circuit to provide another HV shock one minute after the first shock.

Additionally or alternatively, in an embodiment, the method provides for measuring the signal indicative of respiration during normal sinus rhythm to obtain at least one of a baseline peak to peak (P-P) range or a baseline respiratory period; defining a timeout value based on the respiratory period, wherein the gating further comprises setting a timer based on the timeout value, initiating the timer in connection with the declaring the fibrillation episode, the delivering comprising initiating delivery of the HV shock in response to expiration of the timer independent of whether the RG trigger occurs.

It will be readily understood that the components of the embodiments as generally described and illustrated in the Figures herein, may be arranged and designed in a wide variety of different configurations in addition to the described example embodiments. Thus, the following more detailed description of the example embodiments, as represented in the Figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, etc. In other instances, well-known structures, materials, or operations are not shown or described in detail to avoid obfuscation. The following description is intended only by way of example, and simply illustrates certain example embodiments.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the inventive subject matter without departing from its scope. While the dimensions and types of materials described herein are intended to define the parameters of the inventive subject matter, they are by no means limiting and are exemplary embodiments. Many other embodiments will be apparent to one of ordinary skill in the art upon reviewing the above description. The scope of the inventive subject matter should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f) unless and until such claim limitations expressly use the phrase "means for" followed by a statement of function void of further structure.

What is claimed is:

1. A method for managing delivery of a ventricular defibrillation shock, the method comprising:
    providing a subcutaneous implantable medical device (S-IMD) configured to be positioned along a lateral region of a rib cage;

providing a lead coupled to the S-IMD, the lead having subcutaneous extra vascular first and second electrode segments, the first electrode segment configured to be positioned along an anterior of a chest and extend along a side of a sternum, the second electrode segment configured to be positioned along a side of the rib cage and extend laterally in a direction from the side of the sternum in a posterior direction toward a spine;
    sensing cardiac events of a heart;
    utilizing one or more processors to perform:
        declaring at least one of ventricular fibrillation or ventricular tachycardia arrhythmia based on the cardiac events;
        obtaining a respiration proxy signal indicative of respiration, the respiration proxy signal varying over a respiration cycle;
        tracking a respiration state related (RSR) characteristic from the respiration proxy signal related to peak expiration;
        gating delivery of the ventricular defibrillation shock based on occurrence of a respiration-gated (RG) trigger in connection with the RSR characteristic, the RG trigger corresponding to a point in time when the RSR characteristic indicates a select state within the respiration cycle; and
        delivering the ventricular defibrillation shock along a shocking vector between the S-IMD and the first and second electrodes based on the RG trigger to time delivering of the ventricular defibrillation shock to occur during the select state within the respiration cycle, the ventricular defibrillation shock have an amount of energy to treat the at least one of the fibrillation or tachycardia arrhythmia, the select state related to the peak expiration of the respiration cycle.

2. The method of claim 1, wherein the RSR characteristic comprises a slope of the respiration proxy signal and the RG trigger occurs when the slope transitions from a negative value to a positive value, the ventricular defibrillation shock delivered at the peak expiration in the respiration cycle.

3. The method of claim 1, wherein the RSR characteristic represents a minimum amplitude of the respiration proxy signal and the RG trigger occurs when a current level of the respiration proxy signal falls to a select window surrounding the minimum amplitude of the respiration proxy signal corresponding to peak expiration.

4. The method of claim 1, wherein the RSR characteristic represents a respiratory period and the RG trigger occurs when a time period, that corresponds to the respiratory period, elapses following a peak expiration of a most recent breath.

5. The method of claim 1, wherein the RSR characteristic represents a respiratory period and the RG trigger occurs when a time period, corresponding to a select amount of the respiratory period, elapses following a peak inspiration of a most recent breath.

6. The method of claim 1, further comprising: measuring the signal indicative of respiration during normal sinus rhythm to obtain at least one of a baseline peak to peak (P-P) range or a baseline respiratory period; defining a time out value based on the respiratory period, wherein the gating further comprises setting a timer based on the timeout value, initiating the timer in connection with the declaring the at least one of the ventricular fibrillation or ventricular tachycardia arrhythmia, the delivering comprising initiating delivery of the ventricular defibrillation shock in response to expiration of the timer independent of whether the RG trigger occurs.

7. The method of claim 1, further comprising determining the RG trigger by obtaining at least one of thoracic impedance measurements or cardiogenic impedance measurements indicative of the respiratory cycle and obtaining at least one of an estimated respiration depth or respiration phase from the respiratory cycle.

8. The method of claim 1, further comprising obtaining wideband electrogram signals, filtering the electrogram signals for a frequency content indicative of the respiratory cycle, and determining the RG trigger by obtaining at least one of an estimated respiration depth or respiration phase from the respiratory cycle based on the frequency content indicative of the respiration cycle.

9. The method of claim 1, further comprising obtaining an accelerometer signal from an accelerometer, filtering the accelerometer signal to obtain a frequency motion component indicative of a respiratory cycle, and obtaining at least one of an estimated respiration depth or respiration phase from the respiratory cycle.

10. An implantable medical system, comprising:

a lead having subcutaneous first and second electrode segments, the first electrode segment configured to be positioned along an anterior of a chest and extend along a side of a sternum, the second electrode segment configured to be positioned along a side of the rib cage and extend laterally in a direction from the side of the sternum in a posterior direction toward a spine;

a subcutaneous implantable medical device (S-IMD) configured to be positioned along a lateral region of a rib cage, the S-IMD comprising memory and one or more processors, the memory to store program instructions; and the one or more processors that, when executing the program instructions, are configured to:

declare at least one of a ventricular fibrillation or ventricular tachycardia arrhythmia based on sensed cardiac events;

obtain a respiration proxy signal indicative of respiration, the respiration proxy signal varying over a respiration cycle;

track a respiration state related (RSR) characteristic from the respiration proxy signal related to peak expiration;

gate delivery of a ventricular defibrillation shock based on occurrence of a respiration-gated (RG) trigger in connection with the RSR characteristic, the RG trigger corresponding to a point in time when the RSR characteristic indicates a select state within the respiration cycle; and deliver the ventricular defibrillation shock along shocking vector between the S-IMD and the first and second electrode segments based on the RG trigger to time delivering of the ventricular defibrillation shock to occur during the select state within the respiration cycle, the ventricular defibrillation shock having an amount of energy to treat the at least one of the ventricular fibrillation or ventricular tachycardia arrhythmia, the select state related to the peak expiration of the respiration cycle.

11. The system of claim 10, wherein the RSR characteristic comprises a slope of the respiration proxy signal and the RG trigger occurs when the slope transitions from a negative value to a positive value, the ventricular defibrillation shock delivered at the peak expiration in the respiration cycle.

12. The system of claim 10, wherein the RSR characteristic represents a minimum amplitude of the respiration proxy signal and the RG trigger occurs when a current level of the respiration proxy signal falls to a select window surrounding the minimum amplitude of the respiration proxy signal corresponding to peak expiration.

13. The system of claim 10, wherein the RSR characteristic represents a respiratory period and the RG trigger occurs when a time period, that corresponds to the respiratory period, elapses following a peak expiration of a most recent breath.

14. The system of claim 10, wherein the RSR characteristic represents a respiratory period and the RG trigger occurs when a time period, corresponding to a select amount of the respiratory period, elapses following a peak inspiration of a most recent breath.

15. The system of claim 10, wherein the one or more processors are further configured to measure the signal indicative of respiration during normal sinus rhythm to obtain at least one of a baseline peak to peak (P-P) range or a baseline respiratory period; define a time out value based on the respiratory period, wherein the gating further comprises setting a timer based on the time out value, initiate the timer in connection with the declaring the at least one of the fibrillation or tachycardia arrhythmia, and initiate delivery of the ventricular defibrillation shock in response to expiration of the timer independent of whether the RG trigger occurs.

16. The system of claim 10, wherein the one or more processors are further configured to determine the RG trigger by obtaining at least one of thoracic impedance measurements or cardiogenic impedance measurements indicative of a respiratory cycle and obtaining at least one of an estimated respiration depth or respiration phase from the respiratory cycle.

17. The system of claim 10, wherein the electrodes are further configured to obtain wideband electrogram signals, the system further comprising circuitry to filter the electrogram signals for a frequency content indicative of a respiratory cycle, and the one or more processors further configured to determine the RG trigger by obtaining at least one of an estimated respiration depth or respiration phase from the respiratory cycle based on the frequency content indicative of the respiration cycle.

18. The system of claim 10, further comprising an accelerometer to obtain an accelerometer signal, a circuit to filter the accelerometer signal to obtain a frequency motion component indicative of a respiratory cycle, and the one or more processors further configured to obtain at least one of an estimated respiration depth or respiration phase from the respiratory cycle in connection with determining the RG trigger.

19. The method of claim 1, wherein the ventricular defibrillation shock has an energy level between 11 and 50 J.

20. The system of claim 10, wherein the ventricular defibrillation shock has an energy level between 11 and 50 J.

* * * * *